United States Patent
Koyama et al.

(10) Patent No.: US 7,301,053 B2
(45) Date of Patent: Nov. 27, 2007

(54) MODIFIED CYCLIC ALIPHATIC POLYAMINE

(75) Inventors: Takeshi Koyama, Kanagawa (JP); Tetsushi Ichikawa, Kanagawa (JP); Hisayuki Kuwahara, Kanagawa (JP); Masatoshi Echigo, Kanagawa (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 384 days.

(21) Appl. No.: 10/669,701

(22) Filed: Sep. 25, 2003

(65) Prior Publication Data

US 2004/0106684 A1   Jun. 3, 2004

(30) Foreign Application Priority Data

Sep. 26, 2002   (JP) ............................. 2002-280556
Jan. 14, 2003   (JP) ............................. 2003-006126

(51) Int. Cl.
*C07C 211/00*   (2006.01)
(52) U.S. Cl. ...................... 564/305; 564/306
(58) Field of Classification Search ................ 564/305, 564/306
See application file for complete search history.

(56) References Cited

U.S. PATENT DOCUMENTS

| 3,352,913 A | 11/1967 | Schmitt et al. |
| 4,034,040 A | 7/1977 | Cronin et al. |
| 4,751,278 A * | 6/1988 | Brytus ................ 528/88 |
| 4,849,544 A | 7/1989 | Culley et al. |
| 5,679,860 A | 10/1997 | Haas et al. |
| 2002/0055605 A1 * | 5/2002 | Yonehama et al. ........... 528/93 |

FOREIGN PATENT DOCUMENTS

| CZ | 284952 | * | 4/1999 |
| EP | 0 380 029 | | 8/1990 |
| EP | 972786 | * | 1/2000 |
| JP | 48036298 | * | 5/1973 |
| JP | 58017452 | * | 2/1983 |

OTHER PUBLICATIONS

Database WPI, Section Ch, Week 197124 Derwent Publications Ltd., London, Great Britain; Class E14, AN 1971-41876S XP002256787 & JP 46 021857 A (Showa Denko KK).
Patent Abstracts of Japan, vol. 1998, No. 06, Apr. 30, 1998 & JP 10 045878 A (Fuji Kasei Kogyo KK), Feb. 17, 1998.

* cited by examiner

*Primary Examiner*—Yvonne (Bonnie) Eyler
*Assistant Examiner*—Chukwuma Nwaonicha
(74) *Attorney, Agent, or Firm*—Wenderoth, Lind & Ponack, L.L.P.

(57) ABSTRACT

An object of the present invention is to provide a modified cyclic aliphatic polyamine having a low viscosity and a small content of unreacted polyamine which can provide, when it is used as a curing agent for epoxy resin, an epoxy resin composition having an improved workability without adding solvent or diluent and an excellent property of epoxy resin cure product. The above modified cyclic aliphatic polyamine is obtained by addition reaction of a cyclic aliphatic polyamine such as isophoronediamine and norbornanediamine and an alkenyl compound such as styrene. The modified cyclic aliphatic polyamine thus obtained is added in epoxy resin to be used as a curing agent for epoxy resin.

4 Claims, 1 Drawing Sheet

MODIFIED CYCLIC ALIPHATIC POLYAMINE

BACKGROUND OF THE INVENTION

1) Field of the Invention

The present invention relates to a modified cyclic aliphatic polyamine. The present invention also relates to a curing agent for epoxy resin containing the modified cyclic aliphatic polyamine, an epoxy resin composition containing the curing agent for epoxy resin, and an epoxy resin cured product obtained by curing the epoxy resin composition. In the present invention, the term "cyclic aliphatic" includes a cycloaliphatic compound and an aliphatic heterocyclic compound.

The modified cyclic aliphatic polyamine is applicable to a curing agent for epoxy resin and a raw material for curing agent thereof to be utilized in an extremely wide field including application to a coating material such as an electrode position coating for motor car, a heavy-duty anti-corrosion paint for ship, bridge, and land and marine iron structure, and inner coat for drinking can; application to electricity and electronics to be used in household electric products, communication equipments and control systems of motor car and airplane such as a laminated plate, an electric semiconductor sealing compound, an insulating powder coating, and coil impregnation; application to a civil engineering and construction material such as earthquake-proof of bridge, lining, reinforcement and repair of concrete structure, a flooring material of building, lining of water supplying facility and sewerage, and pavement for waste water and permeating water; application to an adhesive for vehicle and airplane, and application to composite materials for airplane, industrial materials and sports equipment and to a chain extender and a raw material for chain extender thereof of a polyurethane resin to be utilized in a very wide field including clothes, sports equipments, home appliances, electronics, medical apparatuses, motor cars, transporting apparatus, civil engineering and construction and industrial materials as foam, elastomer, coating, adhesive, binder, fiber, leather, flooring material, water proof material, athleticmaterial, sealant, coking, medical material and fiber treating agent.

2) Related Art

It has widely known that various polyamines are used as a curing agent for epoxy resin and a raw material for curing agent thereof or a chain extender for polyurethane resin and a raw material for chain extender thereof.

Representative examples of the polyamines are as follows: aliphatic polyamines such as ethylenediamine, diethylenetriamine, triethylenetetramine, tetraethylenepentamine, pentaethylene hexamine, hexamethylenediamine, polyoxypropylenediamine and polyoxypropylenetriamine; alicyclic polyamines such as menthanediamine, isophoronediamine, bis(aminomethyl) cyclohexane, diaminodicyclohexylmethane, bis(4-amino-3-methylcyclohexyl) methane, N-aminomethylpiperazine, and norbornanediamine; aliphatic polyamines having aromatic ring such as xylylenediamine; aromatic polyamines such as phenylenediamine, diaminodiphenylmethane, diaminodiphenylsulfone, and diethyltoluenediamine.

However, these polyamines are scarcely used as it is as a curing agent for epoxy resin without any modifications. In most cases, they are used after various modifications suitable for their own characteristics caused by the reactivity of their amino groups, namely their active hydrogen atoms that each polyamine has, depending on the intended purpose such as an improvement of safety and hygiene, an improvement of workability and imparting of adequate property of cured products suitable for their own application.

Representative methods for a modification of polyamines include 1) a modification by Mannich reaction with a phenol compound and an aldehyde compound, 2) a modification by reaction with an epoxy compound, 3) a modification by reaction with a compound having a carboxyl group, 4) a modification by Michael reaction with an acryl compound and 5) combinations of any of 1) to 4).

By these modifications, a reduction of harmful vapor, an improvement of the property of exothermic reaction at the time of curing and an improvement of an adhesion property, water resistance and chemical resistance of cured products can be achieved.

For example, a curing agent for epoxy resin using isophoronediamine as a raw material has features such that it provides a coating film excellent in both gloss and levelling and a cured product excellent in both water resistance and chemical resistance compared with a curing agent for epoxy resin containing an aliphatic polyamino compound or a curing agent for epoxy resin using an aliphatic polyamino compound as a raw material. (See "New Development Of A Curing Agent For Epoxy Resin" edited by Hiroshi Kakiuchi, published by CMC Co. Ltd., P41-49, May 31, 1994)

In general, a curing agent for epoxy resin is preferable to have a low viscosity from the viewpoint of workability. However, it is known that modified polyamines obtained by various modifications using polyamines as a raw material generally have a high viscosity and poor in workability.

Therefore, in order to achieve the purposes such as a reduction of harmful vapor, an improvement of the property of exothermic reaction at the time of curing and an improvement of an adhesion property, water resistance and chemical resistance of cured products and to obtain a curing agent for epoxy resin having a low viscosity, such method is generally employed that a polyamine is modified by reaction with the modification ratio increased and the reaction product thus obtained is diluted by a solvent and/or diluent to produce a curing agent for epoxy resin. However, a curing agent used for epoxy resin is recently expected to be a non-solvent agent because there is a strong tendency not to use a solvent from the view point of the prevention of global environmental pollution. Thus, since it is desired to prevent the use of a solvent in terms of the environmental problem and the fact that the addition of a diluent is likely to cause the deterioration of the property of an epoxy resin cured product, it is necessary to restrict the addition amount of a solvent and/or diluent.

On the other hand, though it is possible to produce a modified polyamine having a low viscosity by the reaction with the modification ratio decreased, the reaction product thus obtained contains residual unreacted polyamine of the raw material in large quantity and it is difficult to yield good results in a reduction of harmful vapor, an improvement of the property of exothermic reaction at the time of curing and an improvement of an adhesion property, water resistance and chemical resistance of cured products.

Japanese Patent Kokai (Laid-open) No. 2002-161076 refers an amino compound obtained by modifying metaxylylenediamine or the like as a curing agent for epoxy resin and it discloses that this amino compound has a relatively low viscosity.

SUMMARY OF THE INVENTION

An object of the present invention is to provide a modified polyamine having a low viscosity and a small content of unreacted polyamine which can provide, when used as a curing agent for epoxy resin, an epoxy resin composition that impart an excellent property of an epoxy resin cured product.

As a result of extensive studies, the inventors have found that a particular kind of modified cyclic aliphatic polyamine has a low viscosity and a relatively small content of unreacted cyclic aliphatic polyamine and an epoxy resin composition containing a curing agent for epoxy resin comprising the above modified cyclic aliphatic polyamine provides an excellent property of an epoxy resin cured product, and have accomplished the present invention.

That is, the present invention provides a modified cyclic aliphatic polyamine described in the following 1) to 7), an amino compound described in 8) to 11), a curing agent for epoxy resin described in 12) to 13), an epoxy resin composition described in 14) to 15), and an epoxy resin cured product described in 16) to 17).

1) A modified cyclic aliphatic polyamine obtained by addition reaction of a cyclic aliphatic polyamine and an alkenyl compound, wherein the number of carbon atoms in a molecule of the cyclic aliphatic polyamine is at least nine, the number of amino groups in a molecule of the cyclic aliphatic polyamine is at least two and the number of active hydrogen atoms derived from the amino groups is at least three.

2) The modified cyclic aliphatic polyamine according to 1), wherein the number of carbon atoms in a molecule of the polyamine is 9 to 25, the number of amino groups in a molecule of the polyamine is 2 to 5 and the number of active hydrogen atoms derived from the amino groups is at least three.

3) The modified cyclic aliphatic polyamine according to 1), wherein the cyclic aliphatic polyamine is at least one selected from the group consisting of menthanediamine, isophoronediamine, diaminodicyclohexylmethane, bis(4-amino-3-methylcyclohexyl) methane, N-aminomethylpiperazine, norbornanediamine, polycyclohexylpolyamine, and bis(aminomethyl) tricyclodecane; and the alkenyl compound is at least one selected from the group consisting of ethylene, propylene, butene, butadiene, pentene, hexene, heptene, octene, nonene, decene, isobutylene, 2-pentene, 3-methyl-1-butene, 2-methyl-2-butene, 2,3-dimethyl-2-butene, cyclohexene, cyclohexadiene, styrene, and divinylbenzene.

4) The modified cyclic aliphatic polyamine according to 1), wherein the cyclic aliphatic polyamine is at least one selected from the group consisting of isophoronediamine and norbornanediamine.

5) The modified cyclic aliphatic polyamine according to 1), wherein the alkenyl compound is styrene.

6) The modified cyclic aliphatic polyamine according to 4), wherein the alkenyl compound is styrene.

7) The modified cyclic aliphatic polyamine according to 1), wherein the modification ratio of the cyclic aliphatic polyamine by the alkenyl compound is selected from the range wherein the number of active hydrogen atoms derived from the amino groups of the cyclic aliphatic polyamine after modification is more than one.

8) An amino compound represented by the following formula (1).

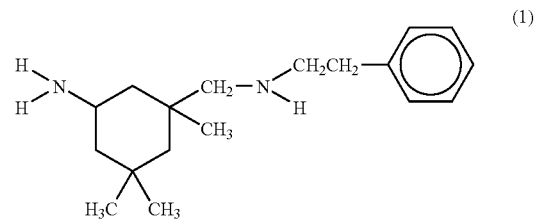

(1)

9) An amino compound represented by the following formula (2).

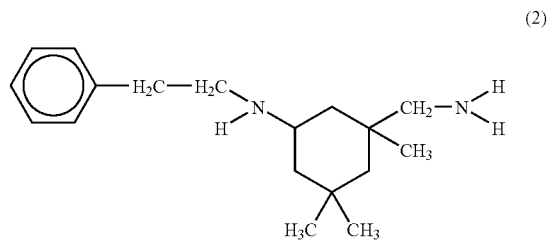

(2)

10) An amino compound represented by the following formula (3).

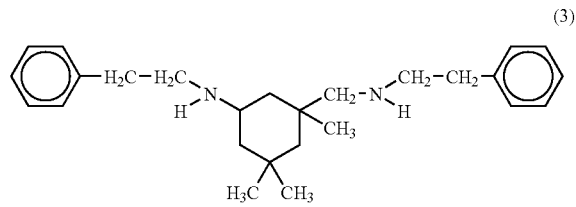

(3)

11) An amino compound represented by the following formula (1), (2) or (3) which is obtained by addition reaction of isophoronediamine and styrene.

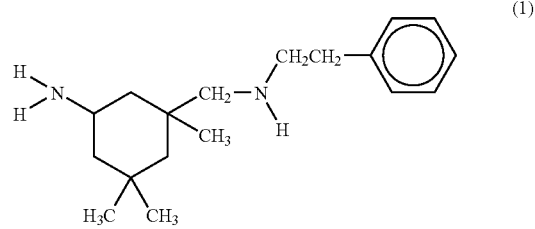

(1)

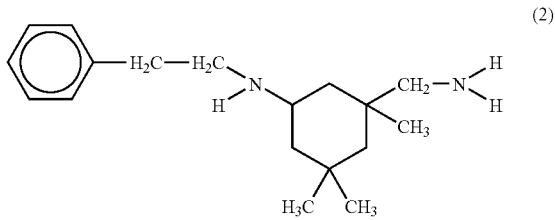

(2)

-continued

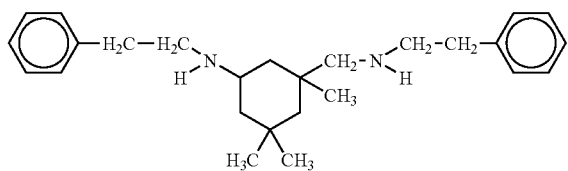
(3)

12) A curing agent for epoxy resin comprising the modified cyclic aliphatic polyamine according to 1).

13) A curing agent for epoxy resin comprising the amino compound according to 8).

14) A curing agent for epoxy resin comprising the amino compound according to 9).

15) A curing agent for epoxy resin comprising the amino compound according to 10).

16) A curing agent for epoxy resin comprising the amino compound according to 11).

17) An epoxy resin composition comprising an epoxy resin and the curing agent for epoxy resin according to 12).

18) An epoxy resin composition comprising an epoxy resin and the curing agent for epoxy resin according to 13).

19) An epoxy resin composition comprising an epoxy resin and the curing agent for epoxy resin according to 14).

20) An epoxy resin composition comprising an epoxy resin and the curing agent for epoxy resin according to 15).

21) An epoxy resin composition comprising an epoxy resin and the curing agent for epoxy resin according to 16).

22) An epoxy resin cured product obtained by curing the epoxy resin composition according to 17).

23) An epoxy resin cured product obtained by curing the epoxy resin composition according to 18).

24) An epoxy resin cured product obtained by curing the epoxy resin composition according to 19).

25) An epoxy resin cured product obtained by curing the epoxy resin composition according to 20).

26) An epoxy resin cured product obtained by curing the epoxy resin composition according to 21).

DETAILED DESCRIPTION OF THE INVENTION

Figure 1:
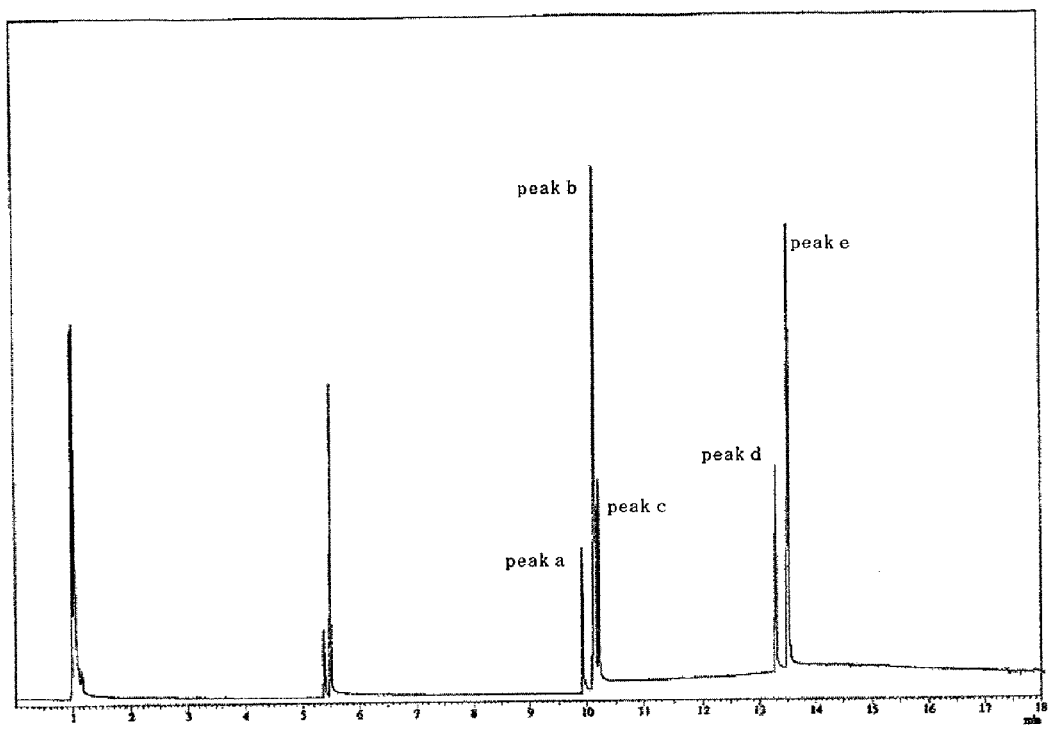
FIG. 1 is a GC-MS chromatogram of the modified cyclic aliphatic polyamine A synthesized in Example 1.

The modified cyclic aliphatic polyamine of the present invention is obtained by addition reaction of a cyclic aliphatic polyamine and an alkenyl compound.

The cyclic aliphatic polyamine to be used in the present invention is a polyamine wherein the number of carbon atoms in a molecule of the polyamine is at least 9, preferably 9 to 25, the number of amino groups in a molecule of the polyamine is at least 2, preferably 2 to 5, and the number of active hydrogen atoms derived from the amino groups is at least 3. Examples of the cyclic aliphatic polyamine include menthanediamine, isophoronediamine, diaminodicyclohexylmethane, bis(4-amino-3-methylcyclohexyl) methane, N-aminomethylpiperazine, norbornanediamine, polycyclohexylpolyamine, and bis(aminomethyl)tricyclodecane, among which isophoronediamine or norbornanediamine is preferable. Bis(aminomethyl)tricyclodecane includes 3(4),8 (9)-bis-(aminomethyl)-tricyclo[5.2.1.0(2,6)] decane and its isomer(s), any of which may be used.

Each of the above polyamines may be used individually or plural of them may be used, among which isophoronediamine and norbornanediamine are particularly preferable.

Further, other polyamino compounds may be mixed to the above cyclic aliphatic polyamine. However, when the amount of other polyamino compounds to be mixed is larger than the amount of cyclic aliphatic polyamine, the features of the modified cyclic aliphatic polyamine of the present invention cannot be maintained. Therefore, it is preferable that the amount of other polyamino compounds is 1 part by mole or below per 1 part by mole of the cyclic aliphatic polyamine of the present invention.

Examples of other polyamino compound to be mixed with the cyclic aliphatic polyamine include aliphatic polyamines such as ethylenediamine, diethylenetriamine, triethylenetetramine, hexamethylenediamine and polyoxyalkylenepolyamine; aromatic polyamines such as metaphenylenediamine, diaminodiphenylmethane and diaminodiphenylsulfone.

As the alkenyl compound to be used in the present invention, any alkenyl compound scan be applied. Among them, an alkenyl compound wherein the number of carbon atoms is 2 to 10 is preferable. Examples of such an alkenyl compound include ethylene, propylene, butene, butadiene, pentene, hexene, heptene, octene, nonene, decene, isobutylene, 2-pentene, 3-methyl-1-butene, 2-methyl-2-butene, 2,3-dimethyl-2-butene, cyclohexene, cyclohexadiene, styrene, and divinylbenzene, among which styrene is particularly preferable.

The modified cyclic aliphatic polyamine in the present invention is obtained by addition reaction (modification) of the above cyclic aliphatic polyamine and the above alkenyl compound. Most preferably, the modified cyclic aliphatic polyamine in the present invention is obtained by addition reaction of a cyclic aliphatic polyamine selected from the group consisting of isophoronediamine and norbornanediamine and styrene.

The addition reaction product thus obtained can be used as a modified cyclic aliphatic polyamine of the present invention directly, i.e., for example, without purification. Therefore, since the liquid of the reaction product usually contains an unreacted cyclic aliphatic polyamine as a residual, it generally is a mixture of an addition product obtained by the addition reaction and an unreacted cyclic aliphatic polyamine.

As for the modification ratio of the cyclic aliphatic polyamine by the alkenyl compound of the present invention, though it can be selected appropriately as usage. For example when the modified cyclic aliphatic polyamine in the present invention is used as a curing agent for epoxy resin, it is preferable to select from the range wherein the number of active hydrogen atoms derived from the amino groups in the cyclic aliphatic polyamine after modification is more than 1. Namely, it is preferable that the number of active hydrogen atoms derived from the amino groups in the cyclic aliphatic polyamine which remains in the modified cyclic aliphatic polyamine without participating in the modification is at least 2.

Another object of the present invention is to provide an amino compound represented by the following formula (1) wherein a phenylethyl group is bound to the methyleneamino group of isophoronediamine, an amino compound represented by the following formula (2) wherein a phenylethyl group is bound to the amino group of isophoronediamine and an amino compound represented by the following formula (3) wherein two phenylethyl groups are bound to the methyleneamino group and the amino group, respectively, of isophoronediamine. These compounds are obtained by addition reaction of isophoronediamine and styrene.

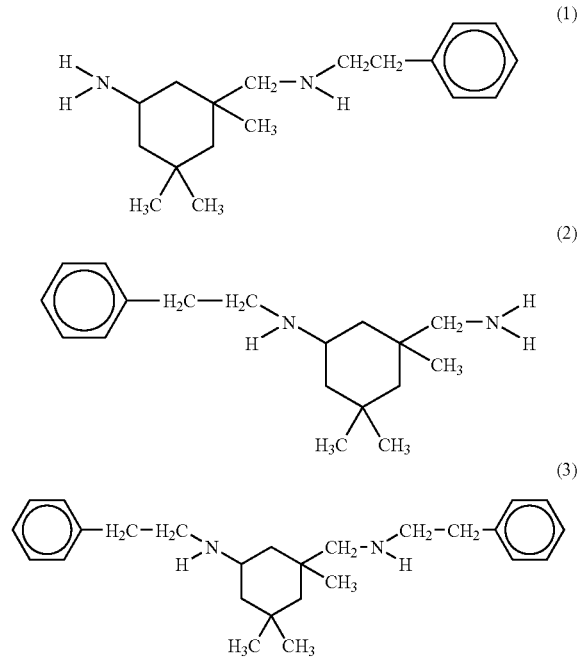

In the present invention, the reaction product obtained by addition reaction of isophoronediamine and styrene can be used as a modified cyclic aliphatic polyamine or an amino compound (hereinafter merely referred to as "a modified cyclic aliphatic polyamine") of the present invention directly as it is.

Thus, more preferably, the modified cyclic aliphatic polyamine of the present invention is a mixture containing at least one selected from the group of amino compounds represented by the formula (1) to (3). In addition, it usually is a mixture which contains unreacted isophoronediamine and the like other than the amino compound(s) selected from the group of the amino compounds represented by the formula (1) to (3).

In order to use the amino compound(s) obtained by the addition reaction of isophoronediamine and styrene as mentioned above as a curing agent for epoxy resin, the total content of the amino compound(s) represented by the formula (1), (2) and (3) is preferably 15% by weight or more, more preferably 30% by weight or more based upon the weight of the curing agent for epoxy resin.

In a process for producing the modified cyclic aliphatic polyamine of the present invention, the reaction proportion of an alkenyl compound to a cyclic aliphatic polyamine is not limited within the condition that gelation can be avoided. When the reaction proportion of an alkenyl compound to a polyamine is low, the amount of an unreacted polyamine becomes large. On the other hand, when the reaction proportion of an alkenyl compound to a polyamine is high, the number of active hydrogen atoms in an amino group becomes small. Therefore, in the case of using an alkenyl compound with one carbon-carbon double bond and a cyclic aliphatic polyamine with four active hydrogen atoms, preferable reaction proportion is usually 0.1 to 4 mol of alkenyl compound and preferably 0.5 to 2 mol of alkenyl compound to 1 mol of cyclic aliphatic polyamine.

Preferable catalyst to be used in the process of synthesizing a modified cyclic aliphatic polyamine of the present invention includes any substance exhibiting strong basicity. Examples of such catalyst include alkaline metal, alkaline metal amide and alkylated alkaline metal. Among them, alkaline metal amide by the general formula MNRR' wherein M is an alkaline metal, N is nitrogen and R and R' are, each independently, hydrogen or an alkyl group, is preferable and lithium amide ($LiNH_2$) is more preferable.

The amount of the catalyst depends on conditions such as species of raw material, reaction proportion and reaction temperature, and is usually 0.05 to 5% by weight and preferably 0.1 to 3% by weight based upon the total weight of raw material. When the amount of catalyst is too small, the reaction rate may decrease, whereas too large, the reaction rate does not increase which is not economical.

The reaction temperature in synthesizing the modified cyclic aliphatic polyamine of the present invention is usually 50 to 130° C. When the reaction temperature is too low, the reaction rate of cyclic aliphatic polyamine and alkenyl compound is slow, whereas too high, a polymer of alkenyl compounds is easily produced as a by-product. Therefore, it is desirable to select the reaction temperature depending on the species of raw material, reaction proportion and the species and amount of catalyst used.

Since a strong base catalyst such as alkaline metal amide readily reacts with moisture or carbon dioxide in air, it is preferable to exclude the influence of moisture and carbon dioxide by carrying out the reaction in the atmosphere of an inert gas such as nitrogen, helium or argon.

Since the reaction of a cyclic aliphatic polyamine and an alkenyl compound of the present invention is an exothermic reaction, it is necessary to control elevation of temperature of the reaction liquid caused by the exothermic reaction in order to maintain the reaction temperature at a constant temperature. Further, in order to inhibit the polymerization of alkenyl compound, it is preferable to add the alkenyl compound dropwise to the reaction liquid within the range of a constant reaction temperature. It is preferable to select the time necessary to add the alkenyl compound dropwise depending on the reaction proportion, the amount of catalyst and the like.

Since the reaction rate is greatly governed by the reaction proportion and the reaction temperature of a cyclic aliphatic polyamine and an alkenyl compound and the species and amount of catalyst, the reaction time should be set depending on the above-mentioned conditions. However, it is preferable to determine a reaction time by taking a sample of the reaction liquid during the reaction and then determining the quantity of the alkenyl compound as the raw material by gas chromatography or liquid chromatography so that a time necessary for the quantity of unreacted alkenyl compound to reach to 1% by weight or below be regarded as the reaction time.

After the completion of the reaction, the reaction liquid thus obtained comprises modified cyclic polyamine synthesized by the reaction and catalyst. There action liquid usually further contains unreacted cyclic aliphatic polyamine and/or unreacted alkenyl compound. When alkaline metal amide is used as catalyst, it is possible to remove the catalyst by filtration. Filtration can be carried out by firstly changing the alkaline metal amide to a readily removable salt thereof by adding acids such as hydrochloric acid, hydrogen chloride gas and acetic acid, alcohols such as methanol and ethanol or water, and then filtrating the salt. For example, when water is used, alkaline metal amide is changed to hydroxide thereof which is easy to filtrate.

The modified cyclic aliphatic polyamine obtained after the above reaction is a clear light yellow-colored liquid having a viscosity of 35 to 3000 mPa·s, preferably 50 to 1000 mPa·s, more preferably 50 to 500 mPa·s at a temperature of 25° C.

When isophoronediamine is selected as a cyclic aliphatic polyamine and styrene is selected as an alkenyl compound in the process of synthesizing a modified cyclic aliphatic polyamine of the present invention, the reaction liquid after completion of reaction and removal of used catalyst usually contains amino compounds such as 1:1 addition reaction product represented by the above formula (1) or (2) wherein 1 molecule of styrene was added to one primary amino group of 1 molecule of isophoronediamine, 1:2 addition reaction product represented by the above formula (3) wherein 2 molecules of styrene were added to two primary amino groups of 1 molecule of isophoronediamine respectively, and others such as 1:3 addition reaction product wherein 2 molecules of styrene were added to one primary amino group and 1 molecule of styrene was added to another primary amino group of 1 molecule of isophoronediamine, 1:4 addition reaction product wherein 4 molecules of styrene were added two by two to each of two primary amino groups of 1 molecule of isophoronediamine, and further contains unreacted isophoronediamine. Among above several kinds of addition products, the content of each addition product in the total amino compounds is governed by the reaction proportion of styrene to isophoronediamine. The higher the proportion of styrene is, the higher the proportion of addition products with a large number of addition molecules becomes.

The modified cyclic aliphatic polyamine of the present invention has reactivity with epoxy resin or isocyanate and is useful as a curing agent for epoxy resin and a chain extender for polyurethane resin. Furthermore, it can be utilized widely in various field such as a paper reinforcing agent, chemicals for rubber, boiler compounds, a slag inhibitor, a surfactant, an emulsifier, a dye, a pigment, a dyeing assistant, an oil solution for fiber, cosmetics, a crease-proofing agent, a chelating agent, a ore floatation agent, a detergent, a thixotropic agent, a pH adjuster, a pesticide, a herbicide, a stabilizer for agricultural chemicals, feed additives, catalyst, a polymerization accelerator, a polymerization inhibitor, a stabilizer, an ion-exchange resin, a gas absorbent, an antioxidant, a corrosion inhibitor, an antirust, a sterilizer, an antibacterial agent, an antifreeze liquid, a lubrication oil, a lubricant, an intermediate of pharmaceuticals, polyamide, a solvent and photographic chemicals.

Particularly, since the modified cyclic aliphatic polyamine has a low viscosity and a small content of unreacted polyamine, when it is applied to a curing agent for epoxy resin, it provides an epoxy resin composition having improved workability without adding solvent or diluent and an excellent property of epoxy resin cured product.

The curing agent for epoxy resin of the present invention which contains the above-mentioned modified cyclic aliphatic polyamine may be used alone or as a mixture with other polyamine-type curing agents for epoxy resin. Though the mixing ratio is not limited as long as it is selected within limits not losing the characteristics of the modified cyclic aliphatic polyamine of the present invention, the preferable amount of the modified cyclic aliphatic polyamine is 5 to 80% by weight based upon the total amount of the curing agent.

The epoxy resin composition of the present invention contains epoxy resin and the above-mentioned curing agent for epoxy resin. As for epoxy resin used for the epoxy resin composition of the present invention, any epoxy resin having glycidyl groups reactive with active hydrogen atoms derived from the amino groups of modified cyclic aliphatic polyamine contained in the curing agent for epoxy resin of the present invention can be used. Examples of such epoxy resin preferably include bisphenol A type epoxy resin and bisphenol F type epoxy resin which may be used alone or as a mixture with each other, though usable epoxy resin is not limited to them.

Though the content of the modified cyclic aliphatic polyamine in an epoxy resin composition is not limited, it is preferable to mix 0.7 to 1.2 active hydrogen equivalent of the modified cyclic aliphatic polyamine based upon the total epoxy equivalent of epoxy resin.

In addition, components for other modification such as filler and plasticizer, components for adjusting fluidity such as diluent and thixotropic agent, and other ingredients such as pigment, leveling agent, and tackifier may be added to the epoxy resin composition of the present invention depending on the intended use.

The epoxy resin composition of the present invention can be cured by well known process to produce an epoxy resin cured product. The curing conditions are not restricted and can be appropriately selected depending on the intended purpose.

The modified cyclic aliphatic polyamine of the present invention can be used, as a raw material of amine in a polyamine-type curing agent for epoxy resin, by carrying out further modification. In this case, the molar number of alkenyl compound participating in modification is not restricted as long as the compound thus obtained contains amino groups having active hydrogen atoms and the characteristics of the modified cyclic aliphatic polyamine of the present invention is not impaired. In addition, the process for modification also is not restricted and any methods utilized for a usual polyamine-type curing agent of epoxy resin can be used.

PREFERRED EMBODIMENT OF THE INVENTION

The present invention will be described in more detail below, referring to Examples which are not intended to limit the scope of the present invention. Analysis of a modified cyclic aliphatic polyamine and evaluation of the property of epoxy resin coating film is carried out by the following method.

[Analysis of a Modified Cyclic Aliphatic Polyamine]

(1) Gas Chromatography-Mass Spectrometry (GC-MS) Analysis

Gas Chromatograph: "GC-17A" manufactured by Shimadzu Corporation.

Mass Spectroscope: "QP5050A" manufactured by Shimadzu Corporation.

Column: "DB-1" manufactured by J&W ; length 15 m, inner diameter 0.25 mm, film thickness 0.1 μm.

Column temperature: 120° C./10 minutes+elevation of temperature at the rate of 10° C./minute+300° C./40 minutes.

[Evaluation of Property of Epoxy Resin Coating Film]

Epoxy resin composition was coated on a steel plate with thickness of 200 μm under the conditions of 23° C. and 50%

RH. Intercoat adhesion is evaluated with the coating film prepared by coating upper layer 1 day after coating lower layer.

a) Appearance:

The appearance of coating film after 7 days of curing is evaluated visually (gloss, clarity, leveling), and by touching with finger (drying characteristics).

b) Intercoat Adhesion:

The coating film after 1+7 days of curing is evaluated referring to X cut-tape method of JIS K 5400.

c) Water Resistance:

Water droplets were dropped on a coating film after 1, 4, and 7 days of curing. Change of the appearance of the coating film passed 1 day after dropping was evaluated visually.

d) Chemical Resistance:

Coated steel plate after 7 days of curing was dipped in each chemicals (sodium hydroxide with the concentration of 10%, sulfuric acid with the concentration of 10%, acetic acid with the concentration of 10%, methanol and toluene) for 7 days under the condition of 23° C. Change of the appearance of the coating film was evaluated visually.

e) Salt Spray Resistance

Salt spray test was carried out based on JIS K 5400. Change of the appearance of the coating film after 7 days of spraying was evaluated visually.

f) Evaluation:

Evaluation was carried out based on the following 4 stages of criteria.

⊚;Excellent, ○;good △;fair X;poor

EXAMPLE 1

681.2 g (4.0 mol) of isophoronediamine, manufactured by Degussa AG (hereinafter, "IPDA") and 3.3 g (0.14 mol) of lithium amide, a reagent manufactured by Merck Ltd., were charged to a 2 L (liter) flask, equipped with an agitator, a thermometer, a nitrogen gas inlet, a dropping funnel and a condenser and its interior temperature was raised to 80° C. in a nitrogen gas stream with stirring. Keeping the temperature at 80° C., 416.8 g (4.0 mol) of styrene, special grade reagent, manufactured by Wako Pure Chemical Industries, Ltd., in Japan was added thereto dropwise over 2.5 hours. After the completion of dropwise addition, its interior temperature was maintained to 80° C. for one hour.

Then, after the reaction liquid was cooled to the room temperature, 25.2 g (1.4 mol) of water as the amount of 10 times equal mol to the charged lithium amide was added thereto and stirred. After separating precipitates in the liquid in flask by filtration, remained water was removed by vacuum distillation, whereby 1032.7 g of modified cyclic aliphatic polyamine A was obtained as a reaction product. The viscosity of the modified cyclic aliphatic polyamine A was 90 mPa·s/25° C. and the content of unreacted IPDA in the modified cyclic aliphatic polyamine A was 16.2% by weight base upon the total weight of the reaction product. The active hydrogen equivalent was 92 and the number of active hydrogen atoms was 3.

As the result of GC-MS analysis of the modified cyclic aliphatic polyamine A thus obtained, five peaks other than the peak of unreacted IPDA were detected. When the five peaks were assumed as peaks a, b, c, d and e in the order of retention time, the peak area ratio was IPDA: 11.2%, peak a: 9.2%, peak b: 33.5%, peak c: 11.1%, peak d: 9.5%, peak e: 25.6%. (See FIG. 1).

From the results of GC-MS analysis of each peak of the peaks a, b, c, d and e, the peak a was identified as a trans form of the amino compound represented by the above formula (1) as the presence of the peaks of 152 m/z, 134 m/z, 124 m/z and 105 m/z other than the peak of 183 m/z (M-91) were detected.

The peak b was identified as a cis form of the amino compound represented by the above formula (1) as the presence of the peaks of 166 m/z, 134 m/z, 124 m/z and 105 m/z other than the peak of 183 m/z (M-91) were detected.

The peak c was identified as the amino compound represented by the above formula (2) as the presence of the peaks of 166 m/z, 105 m/z and 30 m/z ($CH_2=NH_2^+$) other than the peak of 183 m/z (M-91) were detected.

The peaks d and e were identified as the amino compounds represented by the above formula (3) as the presence of the peaks of 258 m/z (M-120) 166 m/z, 154 m/z, 134 m/z and 105 m/z other than the peak of 287 m/z (M-91) were detected.

From the results of GC-MS analysis of each peak of the peaks d and e, the peaks 287 m/z (M-91) and 258 m/z (M-120) of the peak d were detected in the similar peak intensity. On the other hand, the intensity of the peak 287 m/z (M-91) was strong and the intensity of the peak 258 m/z (M-120) was weak in the peak e. Thus, the amino compound represented by the formula (3) has isomers represented by the following formula (4) and (5). In the compound represented by the formula (4), the amino group bound to the cyclohexane ring can easily eliminate by the interaction of 1,3-axial position. Accordingly, the peak d was identified as the compound represented by the formula (4) and the peak e as the compound represented by the formula (5).

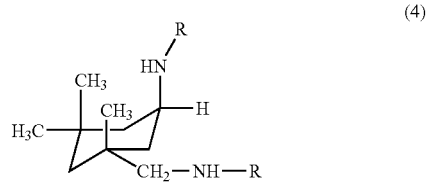

(4)

wherein R is a phenylethyl group

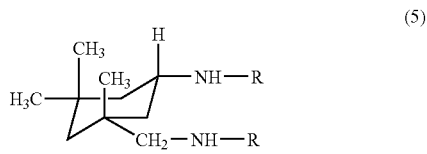

(5)

wherein R is a phenylethyl group

An epoxy resin composition was prepared by mixing bisphenol A type liquid epoxy resin with an epoxy equivalent of 190 g/eq, manufactured by Japan Epoxy Resins Co., Ltd., trade name; Epicoat 828, and the above modified cyclic aliphatic polyamine A as a curing agent for epoxy resin at a ratio shown in Table 1.

The epoxy resin composition thus obtained was cured under the conditions of 23° C. and 50% RH to prepare an epoxy resin cured coating film, and the property of the coating film was evaluated. The evaluation result was shown in Table 1.

EXAMPLE 2

617.2 g (4.0 mol) of norbornanediamine, manufactured by Mitsui Chemicals, Inc. (hereinafter, "NBDA") and 3.1 g (0.14 mol) of lithium amide were charged to a flask similar as the one used in Example 1, and its interior temperature was raised to 80° C. in a nitrogen gas stream with stirring. Keeping the temperature at 80° C., 416.8 g (4.0 mol) of styrene was added thereto dropwise over 2.5 hours. After the completion of dropwise addition, its interior temperature was maintained to 80° C. for one hour.

Then, after the reaction liquid was cooled to the room temperature, 25.2 g (1.4 mol) of water as the amount of 10 times equal mol to the charged lithium amide was added thereto and stirred. After separating precipitates in the liquid in flask by filtration, remained water was removed by vacuum distillation, whereby 969.3 g of modified cyclic aliphatic polyamine B was obtained as a reaction product. The viscosity of the modified cyclic aliphatic polyamine B was 64 mPa·s/25° C. and the content of unreacted NBDA in the modified cyclic aliphatic polyamine B was 15.5% by weight base upon the total weight of the reaction product. The active hydrogen equivalent was 86 and the number of active hydrogen atoms was 3.

An epoxy resin composition was prepared by mixing bisphenol A type liquid epoxy resin with an epoxy equivalent of 190 g/eq, manufactured by Japan Epoxy Resins Co., Ltd., trade name; Epicoat 828, and the above modified cyclic aliphatic polyamine B as a curing agent for epoxy resin at a ratio shown in Table 1.

The epoxy resin composition thus obtained was cured under the conditions of 23° C. and 50% RH to prepare an epoxy resin cured coating film, and the property of the coating film was evaluated. The evaluation result was shown in Table 1.

COMPARATIVE EXAMPLE 1

681.2 g (4.0 mol) of IPDA was charged to a flask similar as the one used in Example 1, and its interior temperature was raised to 80° C. in a nitrogen gas stream with stirring. Keeping the temperature at 80° C., 520.0 g (4.0 mol) of butylglycidylether with an epoxy equivalent of 130 g/eq manufactured by NOF Corporation, trade name; NISSAN EPIOL B, hereinafter "BGE", was added thereto dropwise over 2 hours. After the completion of dropwise addition, its interior temperature was raised to 100° C. and the reaction was carried out for two hours to obtain 1181.4 g of an addition product of IPDA with BGE. The viscosity of the addition product of IPDA with BGE was 3400 mPa·s/25° C. and the content of unreacted IPDA was 15.1% by weight base upon the total weight of the reaction product. The active hydrogen equivalent was 100 and the number of active hydrogen atoms was 3.

An epoxy resin composition was prepared in the same manner as Example 1 using the above addition product of IPDA with BGE as a curing agent for epoxy resin at a ratio shown in Table 1. The epoxy resin composition thus obtained was cured to prepare an epoxy resin cured coating film, and the property of the coating film was evaluated. The evaluation result was shown in Table 1.

COMPARATIVE EXAMPLE 2

1086.8 g of an addition product of NBDA with BGE was obtained by synthesizing in the same manner as Comparative Example 1 except for using 617.2 g (4.0 mol) of NBDA instead of IPDA. The viscosity of the addition product of NBDA with BGE was 1440 mPa·s/25° C. and the content of unreacted NBDA was 14.5% by weight base upon the total weight of the reaction product. The active hydrogen equivalent was 95 and the number of active hydrogen atoms was 3.

An epoxy resin composition was prepared in the same manner as Example 1 using the above addition product of NBDA with BGE as a curing agent for epoxy resin at a ratio shown in Table 1. The epoxy resin composition thus obtained was cured to prepare an epoxy resin cured coating film, and the property of the coating film was evaluated. The evaluation result was shown in Table 1.

TABLE 1

|  | Example 1 | Example 2 | Comparative Example | Comparative Example |
|---|---|---|---|---|
| Epoxy resin composition (g) | | | | |
| Epicoat 828 | 100 | 100 | 100 | 100 |
| Modified cyclic aliphatic polyamine A | 48 | | | |
| Modified cyclic aliphatic polyamine B | | 45 | | |
| Addition product of IPDA with BGE | | | 53 | |
| Addition product of NBDA with BGE | | | | 50 |
| Property of cured coating film | | | | |
| Appearance | | | | |
| Gloss | ◎ | ◎ | ○ | Δ |
| Clarity | ◎ | ◎ | ○ | ○ |
| leveling | ◎ | ◎ | ○ | ○ |
| Drying characteristics | ◎ | ◎ | ○ | ○ |
| Intercoat adhesion | ◎ | ◎ | ○ | ○ |
| Water resistance (1/4/7 days) | ◎/◎/◎ | ◎/◎/◎ | Δ/○/◎ | ○/○/◎ |
| Chemical resistance | | | | |
| 10% sodium hydroxide | ◎ | ◎ | ○ | ○ |
| 10% sulfuric acid | ◎ | ◎ | ○ | ○ |
| 10% acetic acid | ○ | ○ | Δ | X |
| methanol | ○ | ○ | Δ | Δ |
| toluene | ○ | ○ | Δ | Δ |
| Solt Spray Resistance | ◎ | ◎ | Δ | ○ |

As clear from the above Examples, a modified cyclic aliphatic polyamine of the present invention has a low viscosity and the content of unreacted cyclic aliphatic polyamine is relatively small. Thus, the epoxy resin composition containing the above modified cyclic aliphatic polyamine as a curing agent for epoxy resin provides an excellent property of an epoxy resin cured product.

What is claimed is:
1. An amino compound represented by the following formula (1)
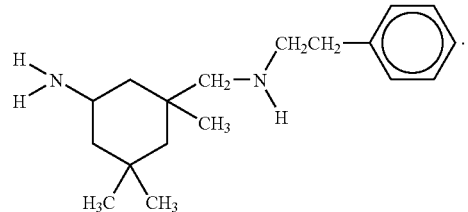
(1)
2. An amino compound represented by the following formula (2)
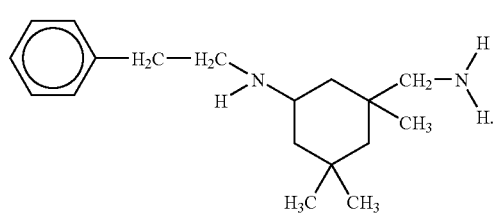
(2)
3. An amino compound represented by the following formula (3)
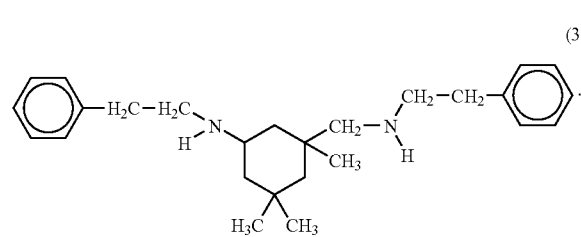
(3)
4. An amino compound represented by the following formula (1), (2) or (3) which is obtained by addition reaction of isophoronediamine and styrene.
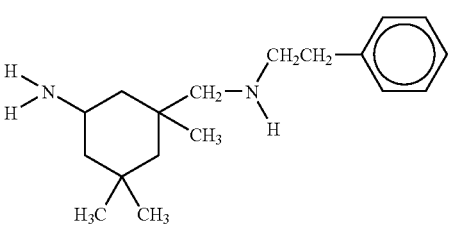
(1)
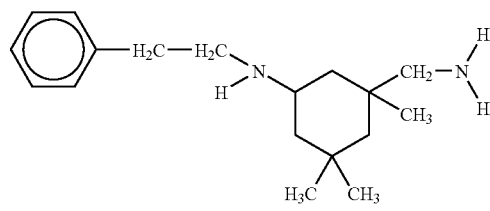
(2)
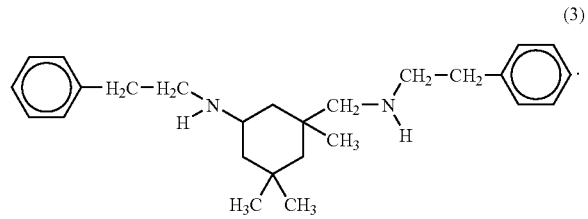
(3)
* * * * *